United States Patent [19]
Reise et al.

[11] Patent Number: 6,080,692
[45] Date of Patent: Jun. 27, 2000

[54] HIGH-STRENGTH, TRANSLUCENT MICA GLASS-CERAMICS

[75] Inventors: Michael Reise, Dreieich-Offenthal; Gerd Mueller, Wuerzburg, both of Germany

[73] Assignee: Fraunhofer-Gesellschaft, Munich, Germany

[21] Appl. No.: 08/952,464

[22] PCT Filed: Mar. 13, 1997

[86] PCT No.: PCT/DE97/00504

§ 371 Date: Feb. 18, 1998

§ 102(e) Date: Feb. 18, 1998

[87] PCT Pub. No.: WO97/34847

PCT Pub. Date: Sep. 25, 1997

[30] Foreign Application Priority Data

Mar. 15, 1996 [DE] Germany .......................... 196 10 300

[51] Int. Cl.⁷ .......................... C03C 10/08; C03C 10/10; C03C 10/16
[52] U.S. Cl. .......................... 501/3; 501/6; 501/8; 501/9; 501/57; 501/59; 501/67; 501/69; 106/35; 433/212.1
[58] Field of Search .................... 501/3, 6, 8, 9, 501/57, 59, 67, 69; 106/35; 433/212.1

[56] References Cited

U.S. PATENT DOCUMENTS

| | | | |
|---|---|---|---|
| 4,652,312 | 3/1987 | Grossman et al. | 501/3 |
| 4,859,634 | 8/1989 | Iwamatsu et al. | 501/3 |
| 5,043,353 | 7/1991 | Shibuya et al. | 501/3 |
| 5,246,889 | 9/1993 | Kasuga et al. | 501/3 |

FOREIGN PATENT DOCUMENTS

| | | |
|---|---|---|
| 0 083 828 | 7/1993 | European Pat. Off. . |
| 37 30 637 | 3/1988 | Germany . |
| 42 07 180 | 9/1992 | Germany . |
| 44 04 921 | 8/1995 | Germany . |
| 5-178641 | 7/1993 | Japan . |

OTHER PUBLICATIONS

S.M. Hoda and G.H. Beall, *Alkaline earth mica glass–ceramics,* pp. 287–300, Adv. in Glasses, Am. Cer. Soc. 1982 (no month).

Uno et al., "Microstructure of Mica–Based Nanocomposite Glass–Ceramics", Journal Am. Ceramics Soc., vol. 76, No. 2, pp. 539–541 (1993) (no month).

Uno et al., "Nanocomposite Machinable Glass–Ceramics", Proc. XVI Int. Conf. on Glass, Bd. Sol. Esp. Ceramic, vol. 31–C4, pp. 72–78 (1992) (no month).

Baik et al., "Mechanical Properties of Mica Glass–Ceramics", Journal Am. Ceramic Soc., vol. 78, No. 5, pp. 1217–22 (1995) (no month).

Patent Abstract of Japan, "Production of Crystallized Glass", 03045534, Feb. 27, 1991 Dec. 7, 1989, 01180907, Osaka Cement Co. Ltd., Takeo et al.

Patent Abstract of Japan, "Glass Ceramic and its Production", 05178641, Jul. 20, 1993 Dec. 27, 1991, 03347460, Hoya Corp., Yoichi.

*Primary Examiner*—Mark L. Bell
*Assistant Examiner*—David Sample
*Attorney, Agent, or Firm*—Foley & Lardner

[57] ABSTRACT

The invention relates to a glass ceramic in which mica and $ZrO_2$ are present in crystallized form, containing:

$K_2O$: 0–9% by weight
$Na_2O$: 0–9% by weight with the condition that $Na_2O$ and $K_2O$ together make up at least about 4% by weight,
$SiO_2$: 35–60% by weight
MgO: 10–25% by weight
$Al_2O_3$: 7–30% by weight
ZrO2: 4–12% by weight
$F^-$: 2–10% by weight which is essentially free of lithium, calcium, strontium and barium, to a process for its production and to its use as a tooth replacement.

18 Claims, No Drawings

HIGH-STRENGTH, TRANSLUCENT MICA GLASS-CERAMICS

The present invention relates to mica glass ceramics which, because of their mechanical properties, are suitable for a wide range of applications, one example of which is a tooth replacement.

Mica glass ceramics are generally known for the fact that they can be processed by cutting. The processibility is made possible by the foliate morphology of micas and the fact that they are easy to cleave.

Like natural micas, the mica crystals in glass ceramics have a broad range of compositions. The intermediate-layer position in the mica structure can be occupied by elements of the alkali and alkaline-earth groups. While occupation by potassium or other heavy alkali elements corresponds more to the frequently occurring natural compositions, it is also possible for micas having alkaline-earth and lithium ions in the intermediate position to crystallize in glass ceramics. However, apart from micas containing Mg, they exhibit the property of appearing to have only limited use for technical applications. On contact with water, the mica structure swells and the glass ceramic inevitably disintegrates [S. N. Hoda, G. H. Beall: "Alkaline earth mica glass-ceramics" in Adv. in Ceramics, Vol. 4, Nucleation and Crystallization in Glasses, Am. Ceram. Soc, Columbus Ohio, 1982]. Full occupation of the tetrahedral position of the mica structure by silicon leads to tetrasilicate micas which likewise crystallize as a mica phase in mica glass ceramics.

The classical properties of mica glass ceramics permit applications in electronics (high resistivity, low dielectric constant) and in vacuum technology (non-porosity). Because mica glass ceramics are biocompatible, they are also used in medicine as a material for bone replacement.

In many cases, however, the comparatively low strength of mica glass ceramic conflicts with the use of this material. Improved strength, in conjunction with good processibility, at least in the desired phases of the production process, would considerably widen the range of application of mica glass ceramic.

The use of mica glass ceramics in restorative dentistry forms part of the background art. EP 0 083 828 B1 describes tetrasilicate mica glass ceramics with increased resistance to discoloration (through the addition of $Al_2O_3$ and $ZrO_2$) for use as dental structure. The corresponding glass ceramic can be used as a prefabricated block in a standard CAD/CAM method in order to make inlays or onlays from it.

The object of the present invention is to provide a mica glass ceramic which has good chemical stability and high mechanical strength, a high degree of translucence and a degree of processibility which is sufficient to allow it to be processed on CAD/CAM machines.

This object is achieved by a glass ceramic in which mica and $ZrO_2$ are present in crystallized form, containing:
$K_2O$: 0–9% by weight
$Na_2O$: 0–9% by weight
with the condition that $Na_2O$ and $K_2O$ together make up at least about 4% by weight,
$SiO_2$: 35–60% by weight
MgO: 10–25% by weight
$Al_2O_3$: 7–30% by weight
$ZrO_2$: 4–12% by weight
$F^-$: 2–10% by weight
which is essentially free of lithium, calcium, strontium and barium.

The proportion of $F^-$ is preferably 4–10% by weight.

"Essentially free" is in this case intended to mean that said elements should be present at most in such proportions as are caused by the introduction of impurities, typically overall less than 1% by weight, preferably less than 0.5% by weight. Above all, the proportion of lithium should preferably be less than 0.1% by weight, since, because of the low molecular weight of Li, a quantity of, for example, as little as 1% by weight of $Li_2O$ has a considerable effect on the properties of the glass ceramic, in particular its resistance to hydrolysis.

Further, extra components for imparting color, for fluorescence or for improving the processing properties of the glass may be added, for example: $CeO_2$, $La_2O_3$, $MnO_2$, $Fe_2O_3$, $TiO_2$, $Y_2O_3$ and $B_2O_3$ in quantities of up to about 5% of each component, and together no more than about 10%. The mixtures are produced in the corresponding proportions from the raw materials (oxides, fluorides,. carbonates, etc.). The mixtures are melted at 1300–1600° C., preferably 1400–1550° C., for, for example, 1–5 hours in a covered crucible while being stirred, then cast in corresponding molds and subsequently cooled to room temperature.

The subsequent conversion of the glass into a glass ceramic takes place by continuous heating of the glasses to crystallization temperature or by heating to a nucleation temperature and subsequently increasing the temperature to crystallization the glasses. The nucleation temperature is about 20–200 K above the transformation temperature, and the nucleation time is about 0.5–3 hours. The crystallization temperature is about 200–450 K above the transformation temperature, and the crystallization time is about 0.5–5 hours.

At least mica crystals and $ZrO_2$ crystals are crystallized during the described heat treatment. It is also possible for secondary phases (cordierite, enstatite, spinel) to crystallize in small quantities.

A high degree of translucence is achieved by the formation of very finely crystalline micas having grain sizes of 0.5–3 $\mu$m. The house-of-cards structure of these very fine micas ensures sufficient processibility.

The strength of the glass ceramic is essentially ensured by the fine-grained micas and the conversion strengthening by tetragonal $ZrO_2$. Tetragonal $ZrO_2$ can undergo stress-induced martensitic conversion into the monoclinic modification. This conversion is associated with an increase in volume by 3–5 percent. As a result, the tip of an incipient crack is placed under pressure and the strength of the material is increased. Other $ZrO_2$ strengthening mechanisms include microcrack strengthening by the formation of microcracks at spontaneously converted $ZrO_2$ grains and consolidation by compressive surface stresses which may be produced by the conversion of the near-surface tetragonal $ZrO_2$ into the monoclinic modification (for example by grinding). According to the invention, it is in this case established that the useful increases in strength can preferably be achieved by the presence of tetragonal $ZrO_2$ crystallites in the size range of from about 20 to about 200 nm.

The mica glass ceramics according to the invention can be processed in various ways.

It is possible to grind prefabricated blocks of the glass ceramic on corresponding CAD/CAM grinders in order to obtain a precisely dimensioned work-piece (see Examples 1 and 2). If better processibility of the glass ceramic is required, the glass ceramic may, in an initially heat-conditioned and readily processible state, be processed by cutting, and the work-piece which is obtained in this way can be consolidated by a subsequent heat treatment, in which case the processibility is reduced but the abrasion resistance at the same time increases (see Example 3).

It is further possible to melt glasses of these compositions and cast them in molten form in a corresponding mold (in the field of dentistry, for example, tooth crowns or bridges) and subsequently to crystallize them to form a glass ceramic.

On account of its mechanical properties, the glass ceramic according to the invention is suitable not only for inlays and onlays, like the materials in EP 0 083 828 B1, but can further, for example, also be used for other forms of tooth replacement (crowns and bridges) since, besides the requisite processibility, for example, in CAD/CAM equipment, it also has high mechanical strength and, with the aid of suitable additives, may also have translucence and coloration corresponding to dental enamel. It further has the chemical stability needed for use as a tooth replacement.

Illustrative embodiments:

Some illustrative embodiments for the novel mica glass ceramics will be given below.

The compositions are given as weighed. The analyzed compositions are further given for some of the glasses. The described strengths were determined using the 4-point bending test (40 mm lower, 20 mm upper support separation) on samples measuring $3 \times 4 \times \geq 45$ mm$^3$. The processibility of the samples means that they can be sawed even using a commercially available hardened steel saw blade. The translucence was determined qualitatively using 3 mm thick samples. In this case, "good" means that a black line on a white background can still be seen through a glass ceramic plate.

EXAMPLE 1

Composition (% by weight)
$SiO_2$: 51.58
$Al_2O_3$: 15.5
MgO: 10.42
$MgF_2$: 8.9
$Na_2O$: 3.5
$K_2O$: 2.7
$ZrO_2$: 7.4
Melting temperature 1500° C./3 hours
1st thermal conditioning: Heating rate 4 K/min, 700° C., 1.5 hours and 970° C., 2.5 hours.
Strength: 265 MPa (+27 MPa)
Translucence: good
Processibility: good

EXAMPLE 2

Composition (% by weight)
$SiO_2$: 53
$Al_2O_3$: 10.5
MgO: 11.5
$MgF_2$: 10.3
$Na_2O$: 1.5
$K_2O$: 6.2
$ZrO_2$: 7.0
Melting temperature 1500° C./3 hours
1st thermal conditioning: Heating rate 5 K/min, 720° C., 1.5 hours and 1030° C., 2 hours.
Strength: 290 MPa (+31 MPa)
Translucence: good
Processibility: good

EXAMPLE 3

| Composition (% by weight) | | Analysis (% by weight) |
|---|---|---|
| $SiO_2$: | 45.04 | n.a. |
| $Al_2O_3$: | 23.42 | 22.7 |
| MgO: | 10.35 | 17.4* |
| $MgF_2$: | 10.18 | 4.94(F.−) |
| $Na_2O$: | 5.01 | 5.12 |
| $ZrO_2$: | 6.0 | 5.94 |

*)analyzed as Mg and calculated to MgO

Melting temperature 1520° C./2.5 hours
1st thermal conditioning: Heating rate 5 K/min, 680° C., 2 hours and 900° C., 1 hour.
Strength: 205 MPa (±46 MPa)
Translucence: very good
Processibility: good
2nd thermal conditioning: Heating rate 5 K/min, 1000° C., 1 hour.
Strength: 268 MPa (±35 MPa)
Translucence: good
Processibility: poor
Alternative 2nd thermal conditioning:
Heating rate 5 K/min, 1000° C., 3 hours.
Strength: 308 Mpa (±19 Mpa)
Translucence: good
Processibility: poor

We claim:

1. Glass ceramic in which mica and $ZrO_2$ are present in crystallized form, comprising:
   $K_2O$ 0–9% by weight
   $Na_2O$ 0–9% by weight with the condition that $Na_2O$ and $K_2O$ together make up at least about 4% by weight,
   $SiO_2$: 35–60% by weight
   MgO: 10–25% by weight
   $Al_2O_3$ 7–30% by weight
   $ZrO_2$: 4–12% by weight
   F$^−$: 2–10% by weight having less than 0.5% by weight of lithium, calcium, strontium, barium and $B_2O_3$ and additionally containing at least one oxide, selected from $CeO_2$, $La_2O_3$, $MnO_2$, $Fe_2O_3$, and $Y_2O_3$ in quantities of up to about 5% by weight of each oxide and in a total proportion of not more than 10% by weight.

2. Glass ceramic according to claim 1, additionally containing components for imparting color, for fluorescence or for improving the processing properties of the glass.

3. A process for producing the glass ceramic of claim 1, comprising mixing starting substances which will produce a glass ceramic having
   $K_2O$ 0–9% by weight
   $Na_2O$ 0–9% by weight with the condition that $Na_2O$ and $K_2O$ together make up at least about 4% by weight,
   $SiO_2$: 35–60% by weight
   MgO: 10–25% by weight
   $Al_2O_3$ 7–30% by weight
   $ZrO_2$: 4–12% by weight, and
   $MgF_2$: 2–10% by weight,
melting the mixed starting substances to about 1300–1600° C., cooling and, subsequently bringing, the molten glass slowly and/or essentially continuously to its crystallization temperature.

4. The process according to claim 3, in which the starting substances are selected from the group consisting of fluorides, oxides, carbonates and other salts which are converted into one or more of said oxides at high temperatures.

5. A process for producing the glass ceramic of claim 1, comprising mixing starting substances which will produce a glass ceramic having $K_2O$ 0–9% by weight $Na_2O$ 0–9% by weight with the condition that $Na_2O$ and $K_2O$ together make up at least about 4% by weight, $SiO_2$: 35–60% by weight MgO: 10–25% by weight $Al_2O_3$ 7–30% by weight $ZrO_2$: 4–12% by weight, and $MgF_2$: 2–10% by weight melting the mixed starting substances at about 1300–1600° C., cooling and, bringing the molten glass slowly and/or essentially continuously to a nucleation temperature and subsequently to its crystallization temperature.

6. A tooth replacement or part thereof comprising a glass ceramic according to claim 1.

7. A tooth replacement or part thereof comprising a glass ceramic in which mica and $ZrO_2$ are present in crystallized form, comprising:

$K_2O$ 0–9% by weight $Na_2O$ 0–9% by weight with the condition that $Na_2O$ and $K_2O$ together make up at least about 4% by weight, $SiO_2$: 35–60% by weight MgO: 10–25% by weight $Al_2O_3$ 7–30% by weight $ZrO_2$: 4–12% by weight $F^-$: 2–10% by weight having less than 0.5% by weight of lithium, calcium, strontium, barium and $B_2O_3$.

8. A tooth replacement according to claims 7, wherein said glass ceramic is processed and/or shaped by a cutting process.

9. A tooth replacement according to claim 7, wherein an initial heat-conditioned glass ceramic shaped body is processed and set by subsequent heat conditioning.

10. A tooth replacement according to claim 7, wherein said glass ceramic is produced from a molten glass being cast in a refractory mold and subsequently subjected to a heat treatment therein.

11. Glass ceramic in which mica and $ZrO_2$ are present in crystallized form, comprising:

$K_2O$ 0–6.2% by weight $Na_2O$ 0–9% by weight with the condition that $Na_2O$ and $K_2O$ together make up at least about 4% by weight, $SiO_2$: 35–60% by weight MgO: 10–25% by weight $Al_2O_3$ 7–30% by weight $ZrO_2$: 4–12% by weight $F^-$: 2–10% by weight having less than 0.5% by weight of lithium, calcium, strontium and barium and additionally containing at least one oxide, selected from $CeO_2$, $La_2O_3$, $MnO_2$, $Fe_2O_3$, and $Y_2O_3$ in quantities of up to about 5% by weight of each oxide and in a total proportion of not more than 10% by weight.

12. A process for producing the glass ceramic of claim 11, comprising mixing starting substances which will produce a glass ceramic having $K_2O$ 0–6.2% by weight $Na_2O$ 0–9% by weight with the condition that $Na_2O$ and $K_2O$ together make up at least about 4% by weight, $SiO_2$: 35–60% by weight MgO: 10–25% by weight $Al_2O_3$ 7–30% by weight $ZrO_2$: 4–12% by weight, and $MgF_2$: 2–10% by weight melting the mixed starting substances to about 1300–1600° C., cooling and, subsequently bringing the molten glass slowly and/or essentially continuously to its crystallization temperature.

13. The glass ceramic of claim 11 wherein the weight percent of $K_2O$ is 0%.

14. The glass ceramic of claim 11, wherein the $Na_2O$ is present.

15. The glass ceramic of claim 11, wherein the $K_2O$ is present in an amount up to 2.7%.

16. A tooth replacement or part thereof comprising a glass ceramic according to claim 11.

17. Glass ceramic according to claim 11, additionally containing components for imparting color, for fluorescence or for improving the processing properties of the glass.

18. A tooth replacement or part thereof comprising a glass ceramic in which mica and $ZrO_2$ are present in crystallized form, comprising:

$K_2O$ 0–6.2% by weight $Na_2O$ 0–9% by weight with the condition that $Na_2O$ and $K_2O$ together make up at least about 4% by weight, $SiO_2$: 35–60% by weight MgO: 10–25% by weight $Al_2O_3$ 7–30% by weight $ZrO_2$: 4–12% by weight $F^-$: 2–10% by weight having less than 0.5% by weight of lithium, calcium, strontium and barium.

* * * * *